(12) United States Patent
Mogg

(10) Patent No.: US 6,676,652 B2
(45) Date of Patent: Jan. 13, 2004

(54) CATHETER ADAPTER

(76) Inventor: Alan David Mogg, 44 Albert Road, Ferndown, Dorset BG22 9HE (GB)

( * ) Notice: Subject to any disclaimer, the term of this patent is extended or adjusted under 35 U.S.C. 154(b) by 0 days.

(21) Appl. No.: 09/920,837

(22) Filed: Aug. 3, 2001

(65) Prior Publication Data

US 2002/0032436 A1 Mar. 14, 2002

(30) Foreign Application Priority Data

Aug. 4, 2000 (GB) .............................. 0019059

(51) Int. Cl.[7] ............................................ A61M 25/16
(52) U.S. Cl. ...................................................... 604/535
(58) Field of Search ............................... 604/533, 534, 604/535, 536, 905

(56) References Cited

U.S. PATENT DOCUMENTS

| | | | |
|---|---|---|---|
| 4,323,065 A | | 4/1982 | Kling |
| 4,405,163 A | * | 9/1983 | Voges et al. ................. 604/536 |
| 4,473,369 A | * | 9/1984 | Lueders et al. ............. 604/533 |
| 5,163,903 A | | 11/1992 | Crittenden et al. |
| 5,330,450 A | * | 7/1994 | Lopez ......................... 604/533 |
| 5,492,147 A | * | 2/1996 | Challender et al. ......... 604/905 |
| 5,505,714 A | | 4/1996 | Dassa et al. |
| 5,620,427 A | | 4/1997 | Werschmidt et al. |
| 5,839,715 A | * | 11/1998 | Leinsing ..................... 604/905 |
| 5,921,968 A | * | 7/1999 | Lampropoulos et al. .... 604/246 |
| 6,039,302 A | * | 3/2000 | Cote et al. .................. 604/905 |

FOREIGN PATENT DOCUMENTS

| | | |
|---|---|---|
| EP | 0422631 A1 | 4/1991 |
| EP | 0661075 A2 | 7/1995 |
| EP | 0 856 332 A1 | 8/1998 |
| EP | 0 930 083 A2 | 7/1999 |
| EP | 0 941 743 A2 | 9/1999 |
| EP | 0 941 743 A3 | 9/1999 |
| EP | 0 930 083 A3 | 10/1999 |
| GB | 1505349 | 3/1978 |
| GB | 2 331 339 A | 5/1999 |
| WO | WO 83/00290 | 2/1983 |

* cited by examiner

*Primary Examiner*—Manuel Mendez
(74) *Attorney, Agent, or Firm*—Burns, Doane, Swecker & Mathis, L.L.P.

(57) ABSTRACT

A catheter adapter comprises an adapter body, a medical device securing means for releasably securing and hermetically sealing the adapter body to a medical device, and catheter securing means for releasably securing and hermetically sealing the adapter body to a catheter of predetermined external diameter, the catheter securing means comprising first and second rigid elements provided with confronting surfaces, and an operating device adapted to urge the rigid elements towards one another, at least one of said confronting surfaces comprising longitudinal channel walls defining a channel, whereby the confronting surfaces combine together to define a close tolerance pathway when the elements are urged towards one another by the operating device, and an operating device retaining means for retaining the operating device in an operative position, the size of the said pathway being such that in use a length of a catheter enclosed within the pathway is compressed and held by engagement of said rigid elements with the catheter, the operating device comprising seal biasing means by which a resilient sealing element is also compressed against the catheter and urged against the adapter body to form a fluid seal therebetween whilst the operating device is in the operative position.

16 Claims, 6 Drawing Sheets

CATHETER ADAPTER

This application claims priority under 35 U.S.C. §§119 and/or 365 to GB 0019059.5 filed in United Kingdom on Aug. 4, 2000; the entire content of which is hereby incorporated by reference.

FIELD OF THE INVENTION

This invention relates to a catheter adapter. The inventive adapter can assist in preventing bacteriological material passing into the sterile fluid pathway.

BACKGROUND TO THE INVENTION

Many medical procedures require the use of tubes or catheters to transmit fluids to or from the patient. Some catheters can be inserted through natural orifices, but others are inserted through needles or other surgical procedures, where the catheter tip can be sited in sensitive and critical organs.

The external ends of these catheters usually require adapters to be fitted so that medical equipment can be attached either for the collection or distribution of fluids. The adapter is required to have means for securely connecting to the catheter and to the medical device with joints that seal against leakage.

Epidural catheters, for example, operate in this manner, whereby a flexible plastics catheter is introduced through a needle into the patients epidural space. After insertion an adapter is fitted to the external end of the catheter which grips and seals against the catheter, the other end of the adapter having a luer lock connector for attachment to a drug delivery system.

Drug bearing fluids can then be administered through the adapter and catheter into the patients epidural space. The security of grip, efficiency of use and the integrity of the sealing arrangements provided by the adapter are important for ensuring that bacteriological matter is not transferred through the adapter connection points into the catheter and epidural space, with serious implications for patient safety.

Prior art epidural adapters generally employ a cylindrical soft resilient element, typically 5 mm outside diameter by 12 mm long, which is captive within the adapter, to seal and grip against the catheter. The catheter is located through the centre of the flexible element and most commonly a screw cap is provided to axially compress the element. Because the element is externally constricted by the connector body, when the element is compressed by the screw cap, the internal pathway of the element is contracted, gripping and sealing against the catheter. Because the axial force applied to the element is perpendicular in direction to the radial gripping force applied by the element to the catheter the mechanism is mechanically inefficient. As catheters are also of resilient material the element is required to radially compress the catheter by a significant amount to achieve an effective grip on the catheter. Consequently the element requires a relatively large axial force and displacement to sufficiently deform the element to grip the catheter.

Because of the dual function to seal and grip the catheter the size and material characteristics of the resilient element have to be selected to fulfill both requirements.

The integrity of the catheter connection is dependent in part on how hard the screw nut is tightened, resulting in variable rates of sealing and grip, with the clinician not necessarily knowing the correct level of tightness required to achieve an adequate connection. Furthermore this type of connection gives no visible indication as to how tight or secure the connection is, and in circumstances where the connection had not been tightened enough, or had been accidentally released no warning of the condition is indicated by the adapter.

As the luer lock connection to the medical device is also a screw type locking action, when attempting to release the medical device the clinician may release the catheter connection by mistake. Under these circumstances reconnection of the catheter would not be safe, and the catheter would have to be withdrawn from the patient, and a new sterile catheter inserted with the attendant cost of the procedure and the risk and distress to the patient.

Furthermore the luer lock connector is such that external parts of the connector immediately adjacent to the sealing faces are exposed to touch, and bacterial contamination can easily build up around the connector hub. When breaking this seal to disconnect a medical device such as a biological filter the bacteriological material can be very close to the sterile fluid pathway, with the potential for infectious material being introduced into the sterile fluid pathway, especially during the reconnection of the medical device.

We are aware of patent specification GL 1505349. This discloses an adapter in which a length of flexible resilient tubing through which the catheter extends is gripped between two hinged members that can be clipped together in an operative position in which a semi-circular retaining member is held against a localized portion of the resilient tubing. Again, the resilient tubing is relied upon both to grip the catheter and to effect a seal therewith.

SUMMARY OF THE INVENTION

According to one aspect of the present invention there is provided a catheter adapter comprising an adapter body, a medical device securing means for releasably securing and hermetically sealing the adapter body to a medical device, and catheter securing means for releasably securing and hermetically sealing the adapter body to a catheter of predetermined external diameter, the catheter securing means comprising first and second rigid elements provided with confronting surfaces, and an operating device adapted to urge the rigid elements towards one another, at least one of said confronting surfaces comprising longitudinal channel walls defining a channel, whereby the confronting surfaces combine together to define a close tolerance pathway when the elements are urged towards one another by the operating device, and an operating device retaining means for retaining the operating device in an operative position, the catheter adapter being such that, in use, each rigid element is moved as a whole towards the other rigid element, the size of the said pathway being such that in use a length of a catheter enclosed within the pathway is compressed and held by engagement of said rigid elements with the catheter, the operating device comprising seal biassing means by which a resilient sealing element is also compressed against the catheter and urged against the adapter body to form a fluid seal therebetween whilst the operating device is in the operative position.

Although it would be possible for only one of the rigid elements to be formed with a channel, preferably both elements are provided with respective longitudinal channels that combine together, in the operative condition, to define the close tolerance pathway.

The elements desirably abut one another in the operative condition, but it would be possible for the elements to be spaced apart by a small amount.

In one embodiment of the invention the means for releasably securing and hermetically sealing the adapter to a medical device is a standard luer lock connection.

The rigid elements are preferably provided with a plurality of transverse ridges protruding into and extending around, or partially around, the longitudinal channels such that when the elements are pressed together the catheter enclosed within the pathway formed by the channels is locally deformed and gripped by the series of ridges.

In one embodiment of the invention the operating means comprises a screw type nut.

In another embodiment of the invention the operating means comprises a lever so arranged that when the connector mechanism is in the open position the lever arm is at an angle to the adapter body, and when the lever arm is rotated fully to secure the catheter it lies substantially parallel to the adapter body, the position of the lever arm providing indication that the catheter is connected.

The releasable securing means is preferably a sleeve located around the adapter body and having means to slide axially within limits with respect to the adapter body, the sliding sleeve also having means to rotate the adapter body, the adapter configuration being such that when the lever arm is fully rotated to secure the catheter a spring acting against the sleeve slides the sleeve over the end of the lever arm releasably securing the lever arm against the adapter body.

The sleeve may engage with the medical device to which the adapter is connected to form a shield around the luer lock connector.

The sleeve around the adapter may be adapted to engage with the medical device to which the adapter is connected to restrict movement of the sleeve thus forming an interlock stopping the release of the catheter connector.

Two adapters in accordance with the invention will now be described by way of example only, with reference to the accompanying drawings.

Rigid elements can each be provided with an element camming formation, with the operating device arranged to urge the rigid elements axially against a body camming formation provided on said body, the co-operation of the camming formations causing the rigid elements to be pressed together as the operating device is moved towards the operative position.

An adapter body can be provided with a stepped bore, and with the element camming formation having a rounded corner on each of the elements, and the body camming formation comprising a pair of shoulders defined by the outer ends of a pair of flats in the larger diameter portion of the body bore.

DESCRIPTION OF PREFERRED EMBODIMENTS

Figure 1:
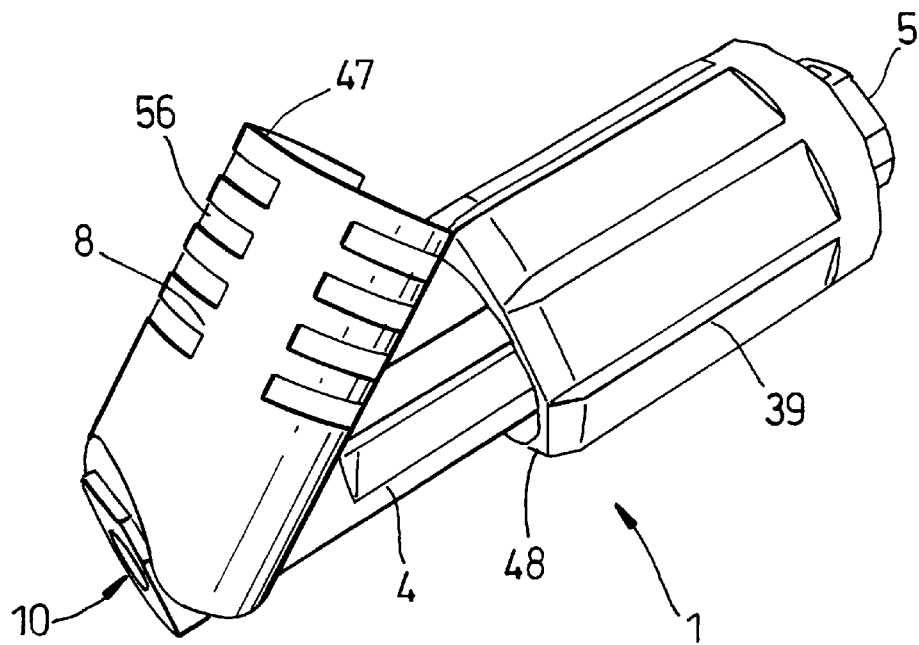
FIG. 1 is a pictorial view of a first adapter in accordance with the invention and shown in an open configuration.
Figure 2:
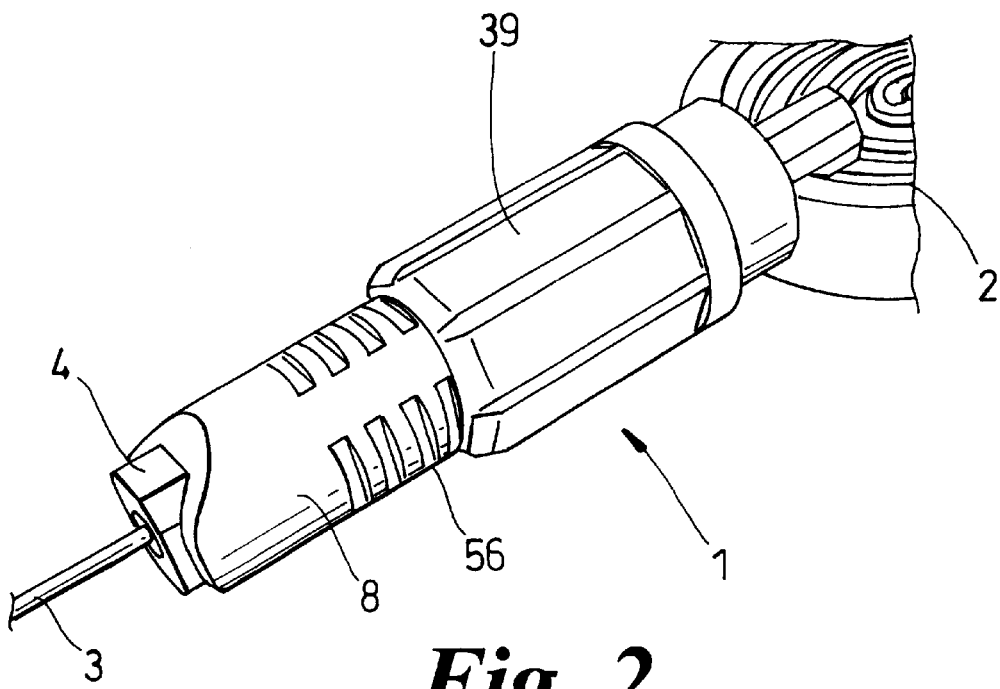
FIG. 2 is a pictorial view of the adapter of FIG. 1 when connected to a catheter and biological filter.

In the Figures, like features and components have like reference numerals.

For the purpose of this description vertical is defined as the plane parallel to the axis of the lever pivot.

For the purpose of this description the adapter is considered 'open' when the catheter connector is in the released position ready to take the catheter.

With reference to FIGS. 1 to 8, an adapter 1, for the connection of biological filter 2 and catheter 3, comprises a rigid plastic body 4 having a standard female luer lock feature 5 at one end, for connection to standard male luer lock feature 6 of filter 2. A rigid plastic lever arm 8 is pivotally attached at the other end of body 4 to operate the catheter connecting mechanism 9. Multiple grip grooves 56 are provided around lever arm 8.

With the lever arm 8 at approximately 45 degrees to body 4, the catheter connecting mechanism 9 is in the open position allowing catheter access to adapter 1 through catheter access hole 10 formed by two identical rigid plastic half collets 11, substantially contained within body 4. A suitable rigid plastic for collets 11 is a polycarbonate. The collets are elongate and their confronting surfaces are formed with respective channels.

Figure 3:
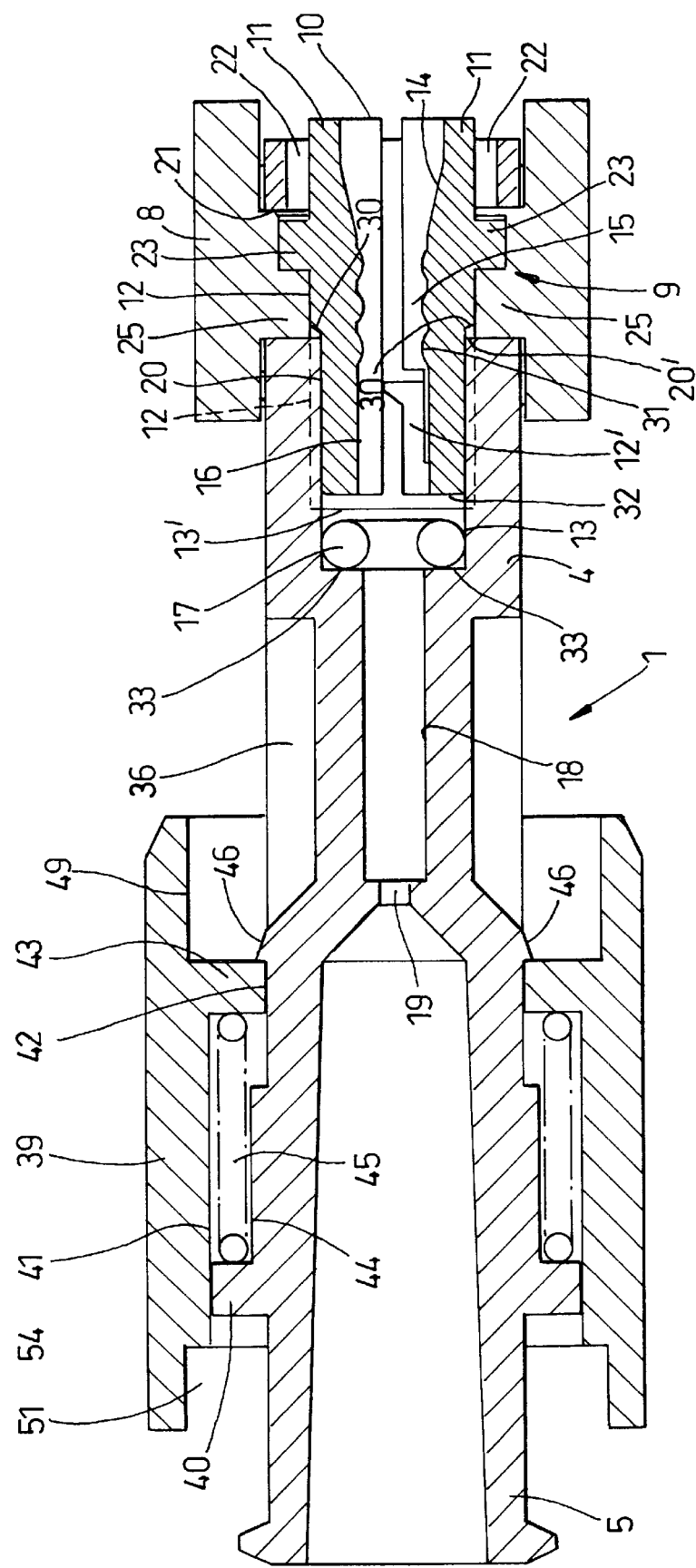
FIG. 3 is a longitudinal cross-section of the adapter of FIG. 1, taken on the horizontal centre line of the body, with the catheter connector open.
Figure 4:
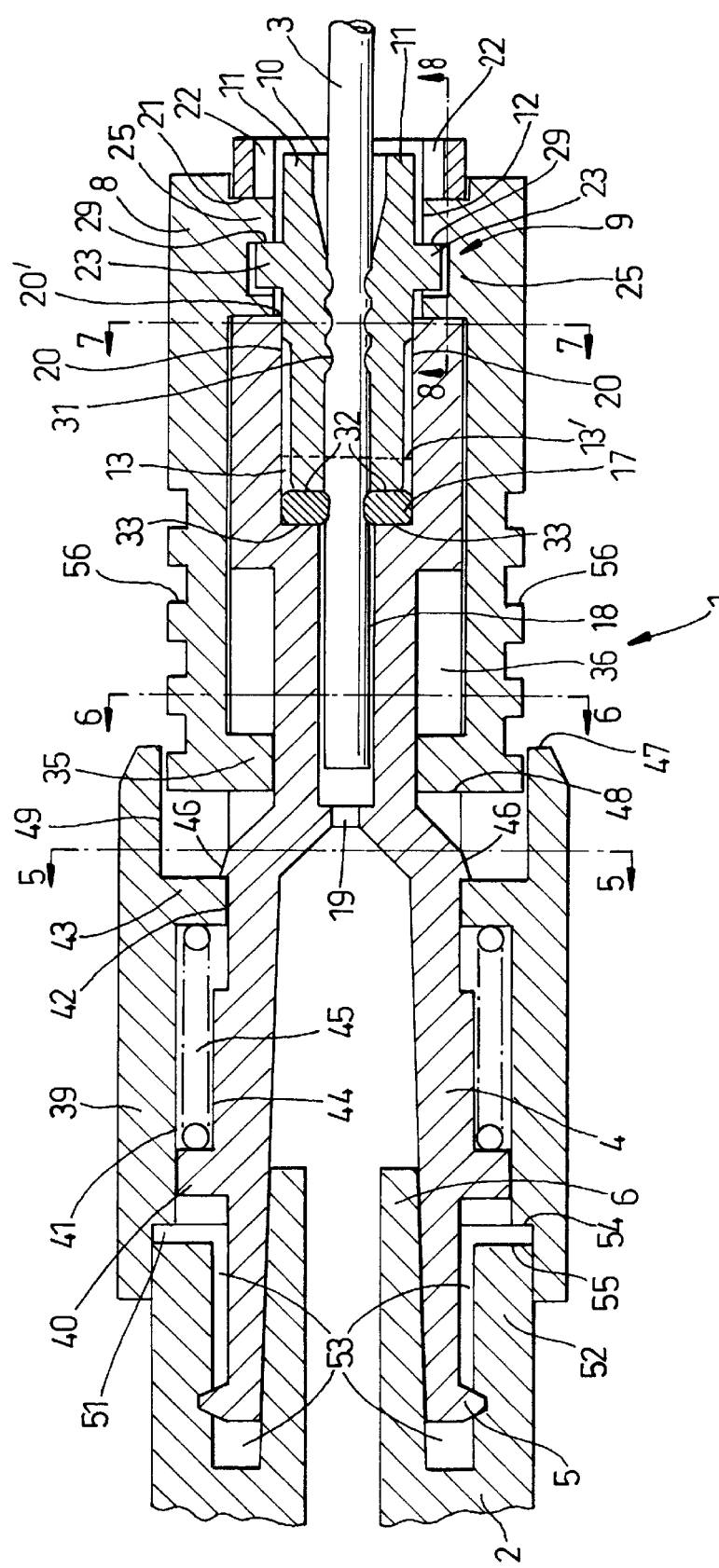
FIG. 4 is a view similar to FIG. 3 but with a catheter and biological filter connected.
Figure 5:
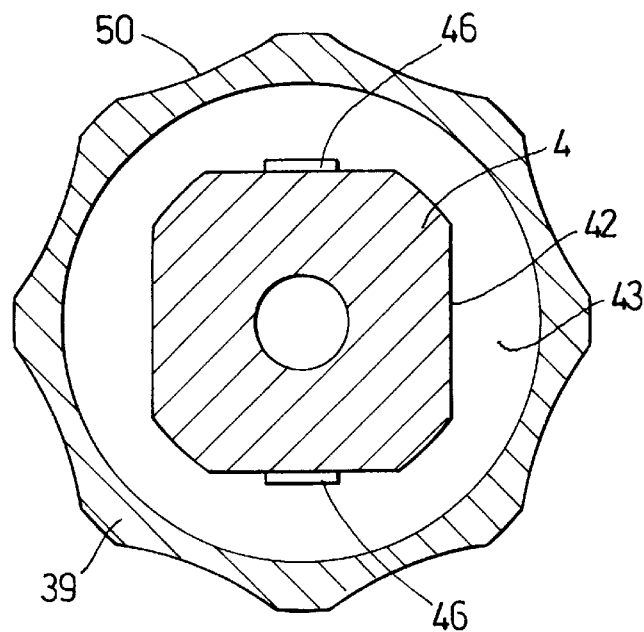
FIG. 5 is a view in section, taken on lines 5—5 of FIG. 4.
Figure 6:
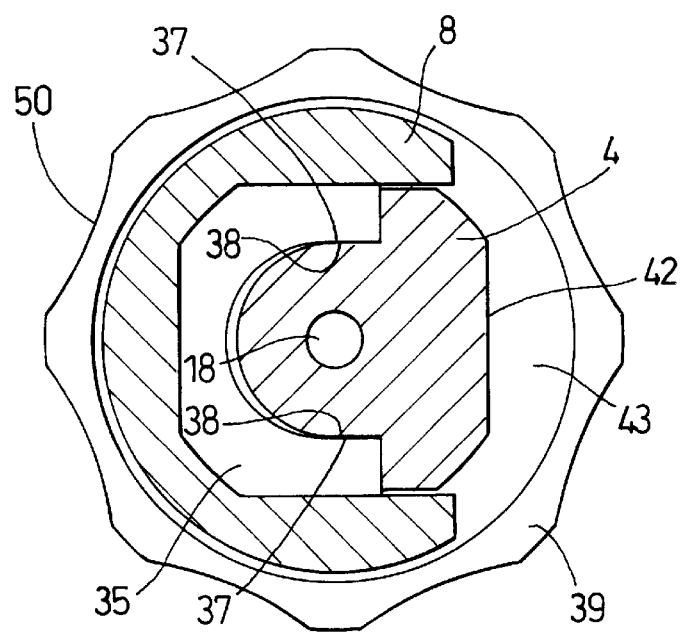
FIG. 6 is a view in section, taken on lines 6—6 of FIG. 4.

When the connector is in the open position, as shown in FIG. 3, the confronting surfaces of the half collets 11 are kept apart by spring arms 12' formed integrally therewith, so that half collets 11 form a stepped cylindrical outer profile of which the larger and smaller ends respectively are contained by, and are of substantially the same diameter as bore portion 12 and bore portion 13 of a stepped bore in body 4. The junction between smaller and larger diameter bore portions 13, 12 respectively define a step 13'.

The close tolerance internal pathway formed by the longitudinal channels of the half collets 11 comprises catheter access hole 10, frusto-conical lead-in section 14, catheter grip section 15 and parallel section 16. At the catheter grip section 15, a series of ridges 31 protrude into and around the respective channels. The radius of the pathway in the absence of said ridges would be substantially the same as the external radius of the catheter to be gripped, the collets 11 being in the condition where they mutually engage one another. Accordingly, the ridges 31 deform the catheter, in the operative condition of the lever arm 8, to grip the catheter firmly.

The diametral spacing between the ridges 31 when the half collets 11 are apart, as in FIG. 3, is sufficient to allow the catheter to pass freely along the pathway.

Bore portion 13 of body 4 also locates '0' ring seal 17, and further bores 18 and 19 complete a pathway through body 4, bore 19 being of a smaller diameter to act as a stop for catheter 3.

Figure 7:
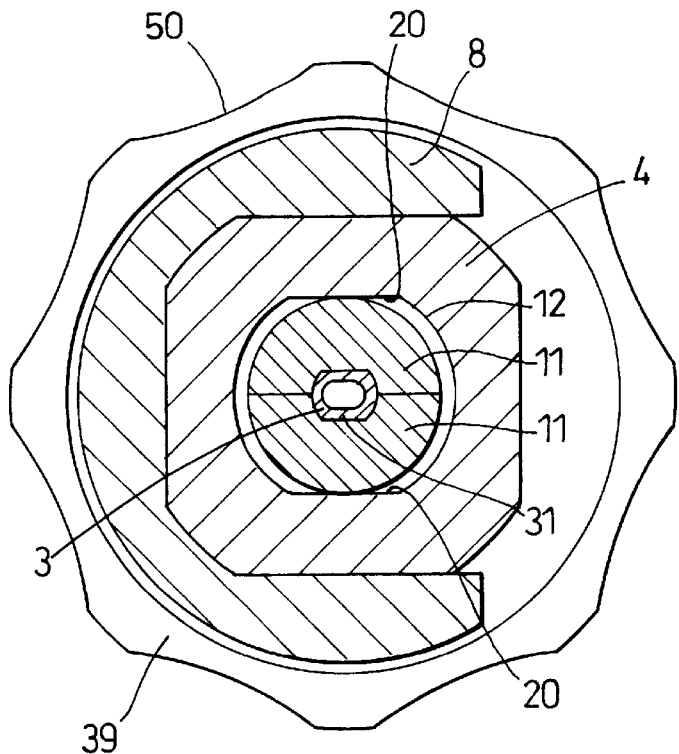
FIG. 7 is a view in section, taken on lines 7—7 of FIG. 4.
Figure 8:
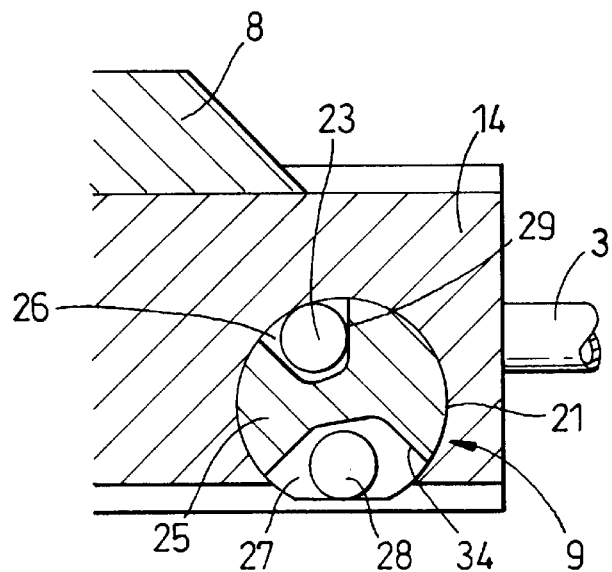
FIG. 8 is a fragmentary cross-sectional view taken on lines 8—8 of FIG. 4.

Part of the bore wall of bore portion 12 at its inner end is filled in to define horizontal flats 20 at both sides, as shown in FIG. 7, the distance between the flats 20 being conveniently the same size as the diameter of the smaller diameter bore portion 13.

Pivot holes 21 in both sides of body 4, have their vertical centre lines below the vertical centre line of body 4. Vertical slots 22 on both sides of the body 4 centre line run into pivot holes 21 allowing access for drive pins 23 of the half collets 11 into the upper part of pivot holes 21.

The lever arm 8 is substantially of a 'C' shape section, with pivot pins 25 on the inside face of the side walls at its end. The pivot pins 25 and side walls are able to spring apart so that pivot pins 25 can locate in, and be retained by, pivot holes 21 of body 4.

A groove 26 cut into pivot pins 25 contains the drive pins 23 of the half collets 11, and a similar groove 27 cut into pivot pins 25 contains pins 28 which are part of body 4 and are upstanding from the bottom face of pivot holes 21.

When lever arm 8 is operated from the open position to connect the catheter, the pivot pins 25 rotate and faces 29 acts upon pins 23, forcing half collets 11 further into body 4. As half collets 11 is pressed into body 4, radius 30 comes into contact with shoulder 20' at the outer end of horizontal flats 20, and the resulting camming action forces both half collets 11 together. The ridges 31 at the catheter grip section 15 locally distort and grip catheter 1. The end face 32 of half collets 11 also compresses '0' seal 17 against face 33 and the catheter 1 to form a fluid seal. End face 32 constitutes a seal biassing means.

On completion of the operation, lever arm 8 lies parallel and substantially enclosing body 4, with stiffening web 35 located in recess 36. Internal faces 37 of web 35 form an interference fit with faces 38 releasably securing the lever arm 8 to body 4.

When lever arm 8 is actuated to release catheter 1, faces 34 of grooves 27 act against pins 28 to limit the movement of the lever arm 8 to approximately 45 degrees to body 4.

Sleeve 39 is located around and supported by body 4, shoulder 40 being a sliding fit within bore 41. Hole 42 in shoulder 43 has square faces with radiuses at the corners, which engages with a similar shape on body 4, such that the sleeve 39 is free to slide axially, but is rotationally keyed to body 4.

Round section 44 supports a compression spring 45 which acts against shoulder 40 and forces shoulder 43 against lugs 46.

When lever arm 8 is actuated from the open position, face 47 comes into contact with edge 48 pushing sleeve 39 clear, and allowing lever arm 8 to come to rest against body 4. Sleeve 39 is then clear to return against lugs 46 by the action of spring 45, enclosing the end of lever arm 8 within bore 49 and releasably securing it.

Adapter 1 is screwed into the luer lock connector of filter 2 by rotating sleeve 39 which in turn rotates body 4, flutes 50 providing rotational grip to sleeve 39. Recess bore 51 engages over the filter luer lock connector part 52 enclosing and shielding a space 53 around the internal parts of the luer lock connector.

Furthermore face 54 of bore 51 and face 55 of luer lock part 52 limit the axial movement of sleeve 39, so that when adapter 1 is connected to filter 2 sleeve 39 cannot be moved sufficiently to release lever arm 8 from bore 49.

In a modification, not illustrated, the sleeve 39 is dispensed with, and instead the free ends of the C-shaped portion are arranged to clip around the body 4, to retain the lever arm 8 in the operative condition.

Figure 9:
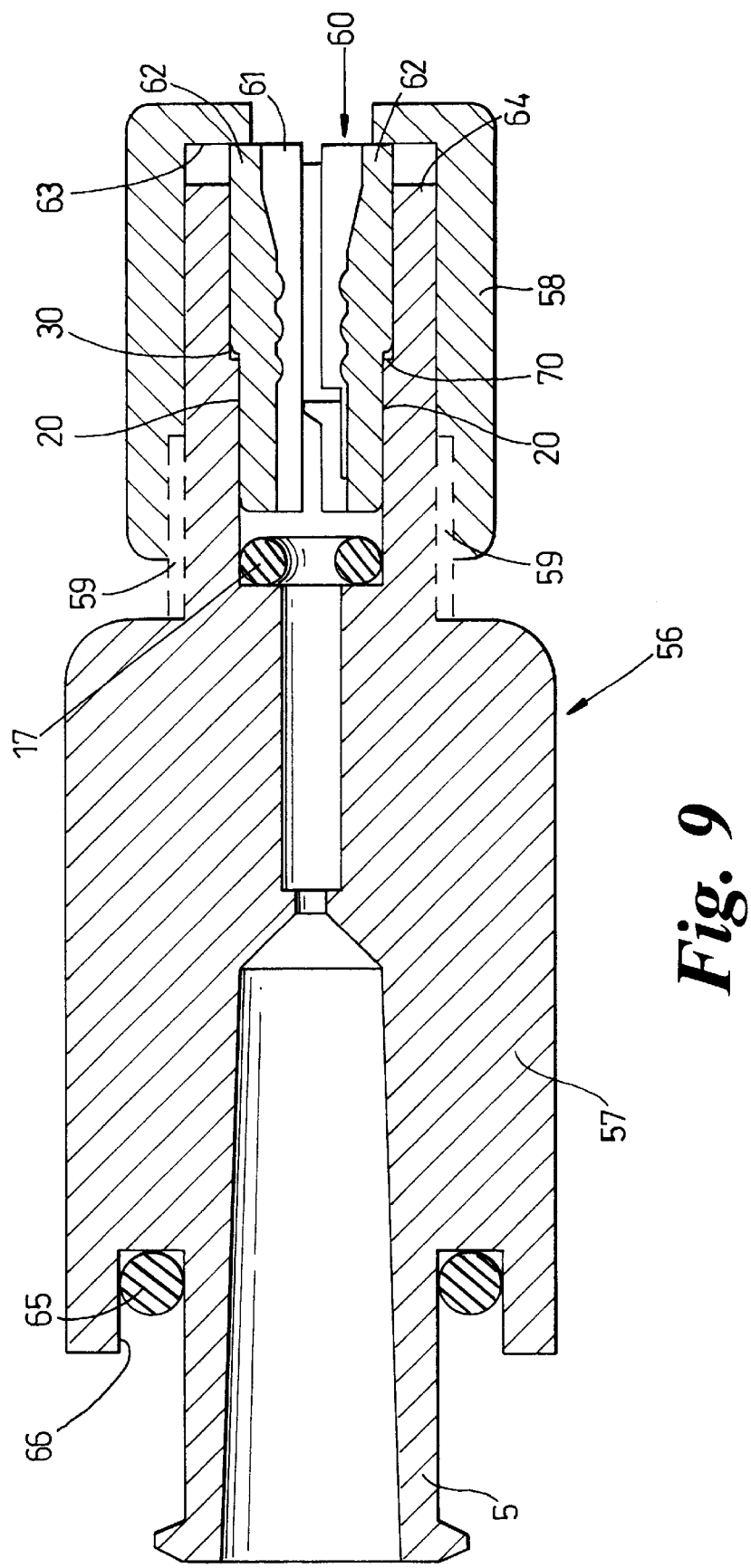
FIG. 9 is a longitudinal cross-section of a second adapter in accordance with the invention, with the catheter connector being shown open.

With reference to FIG. 9, an adapter 56, for the connection of biological filter 2 and catheter 3, comprises a rigid plastic body 57 having a standard female luer lock feature 5 at one end for connection to standard male luer lock feature 6 of filter 7. A rigid plastic open ended screw cap 58 is attached by screw thread 59 to the other end of body 57 to operate the catheter connecting mechanism 60.

With screw cap 58 unscrewed by a small amount from body 57, the catheter connecting mechanism 60 is in the open position allowing catheter access to adapter 56 through opening 61 formed by two identical half collets 62, substantially contained within body 57.

Body 57 has identical internal features to body 4 of FIGS. 1 to 8 but without horizontal slots 22. Half collets 62 have identical features to half collets 11 of FIGS. 1 to 8 but without drive pins 23.

Screw cap 58 is screwed fully in forcing the half collets 62 into body 57. When the radius 30 of the half collets 11 engage step 70, defined by the outer end of flats 20, in body 57, the half collects 62 are urged relatively together to grip the catheter. Thus half collets 62 grip and seal the catheter against body 57 in the same manner as adapter 1 of FIGS. 1 to Face 63 of screw cap 58 comes in contact with face 64 to limit the travel of the screw cap 58 and half collets 62, when a predetermined axial load has been applied to '0' seal 17, so that when fully tightened screw cap 58 is releasably secured to body 57.

'0' seal 65 is a secure fit inside recessed bore 66, which, on connection to a male luer lock connector, provides a fluid seal to protect space 53 around the internal parts of the luer lock connector.

Although in the illustrated embodiments the collets 11 mutually engage with one another in the operative condition, it should be appreciated that it would be possible for the collets to be spaced apart by a small amount if desired in the operative condition.

I claim:

1. A catheter adapter comprising:

an adapter body, a medical device securing means for releasably securing and hermetically sealing the adapter body to a medical device, and catheter securing means for releasably securing and hermetically sealing the adapter body to a catheter of predetermined external diameter, the catheter securing means comprising first and second rigid elements provided with confronting surfaces, and an operating device adapted to urge the rigid elements towards one another, at least one of said confronting surfaces comprising longitudinal channel walls defining a channel, whereby the confronting surfaces combine together to define a close tolerance pathway when the elements are urged towards one another by the operating device, and an operating device retaining means for retaining the operating device in an operative position, wherein, in use, each rigid element is moved as a whole toward the other rigid element such that in use a length of a catheter enclosed within the pathway is compressed and held by engagement of said rigid elements with the catheter, the operating device comprising seal biassing means by which a resilient sealing element is also compressed against the catheter and urged against the adapter body to form a fluid seal therebetween whilst the operating device is in the operative position.

2. An adapter as claimed in claim 1 wherein the rigid elements are elongate and said longitudinal channel walls extend lengthwise of said elongate rigid elements.

3. An adapter as claimed in claim 2 wherein the longitudinal channel walls extend for substantially the full length of said one confronting surface and comprise a tapered lead-in portion.

4. An adapter as claimed in claim 1 wherein said channel walls comprise a plurality of transverse ridges protruding into and extending around the longitudinal channel.

5. An adapter as claimed in claim 1 in which said confronting surfaces of both said elements are formed with said longitudinal channel walls which together define said close tolerance pathway.

6. An adapter as claimed in claim 1 wherein the operating device retaining means comprises a sprung loaded sliding sleeve adapted to releasably secure the operating device in the operative condition.

7. An adapter as claimed in claim 6 wherein, when the adapter is connected to a medical device, the sliding sleeve is prevented by the medical device securing means from being moved to a position in which the operating device is releasable.

8. An adapter as claimed in claim 1 wherein the rigid elements are each provided with an element camming formation, and the operating device is arranged to urge the rigid elements axially against a body camming formation provided on said body, the co-operation of the camming formations causing the rigid elements to be pressed together as the operating device is moved towards the operative position.

9. An adapter as claimed in claim 8 in which said adapter body is provided with a stepped bore, and said element camming formation comprises a rounded corner on each of said elements, and the body camming formation comprises a pair of shoulders defined by the outer ends of a pair of flats in the larger diameter portion of the body bore.

10. An adapter as claimed in claim 1 in which the operating device comprises a lever.

11. An adapter as claimed in claim 10 wherein the lever comprises a lever boss provided with cut-outs which receive trunnion pins on the rigid elements, the lever boss being pivotally mounted in the adapter body.

12. An adapter as claimed in claim 11 in which the pivotal axis of the lever boss is positioned offset from the axis of said pathway.

13. An adapter as claimed in claim 9 in which the operating device is a nut threadedly engaged with the body, the nut abutting with the rigid elements.

14. An adapter as claimed in claim 1 wherein the resilient sealing element is an O-ring seal.

15. An adapter as claimed in claim 7 in which the medical device securing means comprises one part of a luer lock connection, and said sleeve is arranged to extend in use over the other part of the luer lock connection and to engage therewith to provide a biological shield.

16. An adapter as claimed in claim 1 in which the adapter body is adapted to have a luer lock connection with the medical device, the connection comprising a tubular extension on said body which engages around the medical device connection to provide a biological shield.

* * * * *